(12) United States Patent
Kaneko et al.

(10) Patent No.: US 8,592,598 B2
(45) Date of Patent: Nov. 26, 2013

(54) METHOD OF PRODUCING A CRYSTAL OF AN IMIDAZOLE COMPOUND

(75) Inventors: Masayoshi Kaneko, Takarazuka (JP); Shigeo Yabuno, Osaka (JP); Kenji Iwaoka, Osaka (JP); Hidetoshi Nishimura, Hikari (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 820 days.

(21) Appl. No.: 11/662,740

(22) PCT Filed: Sep. 13, 2005

(86) PCT No.: PCT/JP2005/017222
§ 371 (c)(1),
(2), (4) Date: Apr. 16, 2008

(87) PCT Pub. No.: WO2006/030936
PCT Pub. Date: Mar. 23, 2006

(65) Prior Publication Data
US 2008/0262235 A1    Oct. 23, 2008

(30) Foreign Application Priority Data

Sep. 13, 2004 (JP) ................................. 2004/265717

(51) Int. Cl.
*C07D 401/12* (2006.01)
(52) U.S. Cl.
USPC ..................................................... 546/273.7
(58) Field of Classification Search
USPC ..................................................... 546/273.7
See application file for complete search history.

(56) References Cited

U.S. PATENT DOCUMENTS

| | | |
|---|---|---|
| 4,268,397 A | 5/1981 | Horie et al. |
| 6,002,011 A * | 12/1999 | Kato et al. ................. 546/273.7 |
| 7,662,968 B2 * | 2/2010 | Kotar-Jordan et al. .... 546/273.7 |
| 2002/0183363 A1 | 12/2002 | Loebermann et al. |
| 2005/0020638 A1 * | 1/2005 | Singer et al. .................. 514/338 |

FOREIGN PATENT DOCUMENTS

| | | | |
|---|---|---|---|
| EP | 0 174 726 | 3/1986 | |
| EP | 0 302 720 | 8/1989 | |
| EP | 0 944 617 B1 | 9/1999 | |
| JP | 54-12149 | 1/1979 | |
| JP | 04-021519 A | 1/1992 | |
| JP | 05-18926 | 1/1993 | |
| JP | 2000-157983 | 6/2000 | |
| JP | 2000-157984 | 6/2000 | |
| JP | 2001-139569 A | 5/2001 | |
| JP | 2002-250736 | 9/2002 | |
| JP | 2004-2230 | 1/2004 | |
| JP | 2004-002230 * | 8/2004 | ........... C07D 401/12 |
| WO | 91/18895 A1 | 12/1991 | |
| WO | WO-01/30765 A2 | 5/2001 | |
| WO | WO-03/082857 A2 | 10/2003 | |
| WO | WO-2004/046135 A1 | 6/2004 | |

OTHER PUBLICATIONS

English translation of JP 2000-157983 A (which was cited in an IDS filed on Jun. 19, 2007).
English translation of JP 2000-157984 A (which was cited in an IDS filed on Jun. 19, 2007).
English translation of JP 5-18926 A (which was cited in an IDS filed on Jun. 19, 2007).
Office Action issued in corresponding JP Application No. 535242/2006 and English translation thereof (Nov. 29, 2011).

* cited by examiner

*Primary Examiner* — Yong Chu
*Assistant Examiner* — Karen Cheng
(74) *Attorney, Agent, or Firm* — Edwards Wildman Palmer LLP; George W. Neuner (57) ABSTRACT

The instant invention describes a method of producing a crystal of an imidazole compound or a salt thereof, which comprises suspending a solvate of the imidazole compound into a solution containing water, alcohol, and a basic substance.

3 Claims, 2 Drawing Sheets

METHOD OF PRODUCING A CRYSTAL OF AN IMIDAZOLE COMPOUND

TECHNICAL FIELD

The present invention relates to a method for producing an oxidized compound in a chemical/pharmaceutical field, with which a target oxidized compound is produced by an oxidation reaction, and more specifically relates to a method for producing an oxidized compound suitable for an industrial, large-scale production. In particular, the invention relates to a method for producing an oxidized compound, where the method is suitably used for producing a 2-(2-pyridyl- or phenyl-methylsulfinyl)imidazole compound (e.g., see U.S. Pat. No. 4,255,431, European Unexamined Patent Publication No. 45,200, European Unexamined Patent Publication No. 74,341, European Unexamined Patent Publication No. 80,602, European Unexamined Patent Publication No. 5,129, European Unexamined Patent Publication No. 174,726, European Unexamined Patent Publication No. 175,464, United Kingdom Unexamined Patent Publication No. 2,134, 523A, Pamphlet of International Publication WO 01/83,473) which is useful as an antiulcer agent and to a production apparatus for carrying out the method.

BACKGROUND ART

In the past, in the industrial production process comprising an oxidation step, in order to carry out a next step after terminating the oxidation step, an end point of the oxidation reaction is assessed while confirming the amount of an unreacted residue of the starting material with the use of a thin layer chromatography or the like, and the next treatment is carried out. For example, as the method for producing a 2-(2-pyridylmethylsulfinyl)benzimidazole compound among various products produced by oxidation, there has known a method of oxidizing a corresponding 2-(2-pyridylmethylthio)benzimidazole compound with meta chloro perbenzoic acid (e.g., see U.S. Pat. No. 4,255,431 and European Unexamined Patent Publication No. 80,602).

As the method for obtaining sulfoxide from sulfide in general, there has been known a method of oxidizing with the use of peroxy acid, hydrogen peroxide, iodosobenzene, N-halosuccinimide, tertiary butyl hypochlorite, sodium metaperiodate, selenium dioxide, bromine, chlorine, or ozone (e.g., see The Chemistry of Ethers, Crown Ethers, Hydroxyl Groups and Their Sulphur Analogues, Supplement E, Part 1, pp. 539-608, Saul Patai, Ed., John Wiley and Sons, An Interscience Publication, (1980); and Synthesis of Sulfoxides by Oxidation of Thioethers, Michel Madesclaire Ed., Tetrahedron Report Number 210, Tetrahedron, 42, 5459-5495 (1986)), and the like.

In addition, there has been described a method of producing a 2-2(pyridylmethylsulfinyl)benzimidazole compound in the presence of a vanadium compound with the use of hydrogen peroxide as an oxidizing agent in Japanese Unexamined Patent Publication No. 1-131176.

However, it is not easy to determine the end point of the oxidation reaction in the reaction of oxidizing a 2-(2-pyridylmethylthio)benzimidazole compound to produce a 2-(2-pyridylmethylsulfinyl)benzimidazole compound with the use of any oxidizing agent and as well as in the oxidation reactions of obtaining other oxidized compounds, and thus in an industrial production process, the end point of the oxidation reaction is determined to move on to the next step by confirming the amount of an unreacted residue of the starting material with the use of a thin layer chromatography (hereinafter, also may be referred to as TLC). Therefore, it is not a method advantageous for an industrial production, and the production method which more simply determines the end point of the oxidation reaction and swiftly moves on to the next step has been demanded.

The present inventors have conducted extensive studies to discover a production method advantageous in an industrial practice, with which 2-(2-pyridyl- or phenyl-methylsulfinyl) imidazoles can be produced from 2-(2-pyridyl- or phenyl-methylthio)imidazoles in good yield, less amount of byproducts such as corresponding sulfone products and 2-(2-pyridyl- or phenyl-methylsulfonyl)imidazole-N-oxides produced by overreaction are produced, and a computational management or the like is possible. Accordingly, they found that the electric potential for the oxidation of the 2-(2-pyridyl- or phenyl-methylthio)imidazoles to 2-(2-pyridyl- or phenyl-methylsulfinyl)imidazoles increases as the reaction proceeds and rapidly decreases as the reaction comes to the end, and as a result of the further investigation, they have completed the invention.

DISCLOSURE OF THE INVENTION

That is, the invention provides:

(1) a method of producing an oxidized compound which includes measuring an electric potential of an oxidation reaction solution for producing an oxidized compound by an oxidation reaction, and determining an end point of the oxidation reaction on the basis of a predefined decrease of the electric potential;

(2) the production method described in above (1), which determines, after the electric potential of the oxidation reaction solution is reached to a highest electric potential, a point where the amount of an electric potential dropped from the highest electric potential reaches the predefined amount of an electric potential as the end point of the oxidation reaction;

(3) the production method described in above (1) or (2), which further includes introducing an oxidation reaction terminating agent to the oxidation reaction solution immediately after determining the end point of the oxidation reaction;

(4) the method described in any of above (1) to (3), wherein the oxidation reaction is an oxidation reaction of sulfide to sulfoxide;

(5) the production method described in any of above (1) to (4), wherein an imidazole compound represented by the general formula (I'):

[wherein ring C' represents a benzene ring optionally having substituent(s) or a monocyclic aromatic heterocyclic ring optionally having substituent (s); $R^0$ represents a hydrogen atom, an aralkyl group optionally having substituent (s), an acyl group, or an acyloxy group; $R^1$, $R^2$, and $R^3$, are same as or different from each other and each represents a hydrogen atom, an alkyl group optionally having substituent(s), an alkoxy group optionally having substituent(s), or an amino group optionally having substituent(s); and Y represents a nitrogen atom or CH] or a salt thereof is oxidized to produce an oxidized compound of an imidazole compound represented by the general formula (II'):

[wherein ring C', $R^0$, $R^1$, $R^2$, $R^3$, and Y have the same meaning as defined above] or a salt thereof;

(6) the method described in any of above (1) to (4), wherein an imidazole compound represented by the general formula (I):

[wherein ring A is optionally substituted; $R^0$ represents a hydrogen atom or an N-protecting group; $R^1$, $R^2$, and $R^3$, are same as or different from each other and each represents a hydrogen atom, an alkyl group which may be fluorinated, or an alkoxy group which may be fluorinated; and Y represents a nitrogen atom] or a salt thereof is oxidized to produce an oxidized compound of an imidazole compound represented by the general formula (II)

[wherein, ring A, $R^0$, $R^1$, $R^2$, $R^3$, and Y have the same meaning as defined above] or a salt thereof;

(7) the production method described in above (6), wherein the imidazole compound represented by the general formula (II) or a salt thereof is lansoprazole or a salt thereof or an optically active substance thereof;

(8) an apparatus for producing an oxidized compound having a reactor for carrying out an oxidation reaction, an oxidation reduction potential detection means for detecting the value of an oxidation reduction potential of an oxidation reaction solution in the reactor, and a determination means for monitoring at all time the detected values of the oxidation reduction potential detected by the oxidation reduction potential detection means and determining a point where the amount of an electric potential dropped from a highest electric potential of the oxidation reduction potential reaches the predefined amount of an electric potential, as an end point of the oxidation reaction;

(9) the apparatus for producing an oxidized compound described in above (8), which further has a determined result informing means for informing a result determined by the determination means to an operator;

(10) the apparatus for producing an oxidized compound described in above (8), which further has an oxidation reaction terminating agent tank for storing an oxidation reaction terminating agent and a supplying means for supplying the oxidation reaction terminating agent from the oxidation reaction terminating agent tank to the reactor, and outputting a command signal to the supplying means so as to supply the oxidation reaction terminating agent from the oxidation reaction terminating agent tank to the reactor when the determination means determines the end point of the oxidation reaction;

(11) a method of producing a remarkably stable crystal of an imidazole compound represented by the general formula (II')

[wherein ring C' represents a benzene ring optionally having substituent (s) or a monocyclic aromatic heterocyclic ring optionally having substituent (s); $R^0$ represents a hydrogen atom, an aralkyl group optionally having substituent (s), an acyl group, or an acyloxy group; $R^1$, $R^2$, and $R^3$, are same as or different from each other and each represents a hydrogen atom, an alkyl group optionally having substituent(s), an alkoxy group optionally having substituent(s), or an amino group optionally having substituent (s); and Y represents a nitrogen atom or CH] or a salt thereof, which comprises suspending a solvate of the imidazole compound represented by the general formula (II') or a salt thereof into a solution having pH of about 7 to 11;

(12) a method of producing a remarkably stable crystal of an imidazole compound represented by the general formula (II')

[wherein ring C' represents a benzene ring optionally having substituent (s) or a monocyclic aromatic heterocyclic ring optionally having substituent (s); $R^0$ represents a hydrogen atom, an aralkyl group optionally having substituent (s), an acyl group, or an acyloxy group; $R^1$, $R^2$, and $R^3$, are same as or different from each other and each represents a hydrogen atom, an alkyl group optionally having substituent(s), an alkoxy group optionally having substituent(s), or an amino group optionally having substituent (s); and Y represents a nitrogen atom or CH] or a salt thereof, which comprises suspending a solvate of the imidazole compound represented by the general formula (II') or a salt thereof into a solution containing water, alcohol, and a basic substance;

(13) the production method described in above (11) or (12), wherein the imidazole compound represented by the general formula (II') or a salt thereof is lansoprazole or a salt thereof;

(14) the production method described in above (12), wherein the basic substance is ammonia; and (15) the production method described in above (14), wherein the pH of the solution containing water, alcohol, and ammonia is about 8 to 9.

BEST MODE FOR CARRYING OUT THE INVENTION

Hereinafter, the invention will be explained in more detail.

The method of producing an oxidized compound of the invention is characterized in that an electric potential of an oxidation reaction solution for producing an oxidized compound is measured and then an end point of the oxidation reaction is determined on the basis of a predefined decrease of the electric potential, and preferably that when the electric potential of the oxidation reaction solution reaches to a highest electric potential, a point where the amount of an electric potential dropped from the highest electric potential reaches the predefined amount of an electric potential is determined as the end point of the oxidation reaction.

An example of the oxidation reaction which can be applied for the invention include an oxidation reaction of obtaining a methylsulfinyl-substituted imidazole compound (hereinafter, referred to as compound (II')) having an aromatic heterocyclic ring such as pyridine or a benzene ring which may be substituted, from a methylthio-substituted imidazole compound represented by the following general formula (I') (hereinafter, referred to as compound (I')) having an aromatic heterocyclic ring such as pyridine or a benzene ring which may be substituted, with the use of an oxidizing agent.

[wherein ring C' represents a benzene ring optionally having substituent (s) or a monocyclic aromatic heterocyclic ring optionally having substituent (s); $R^0$ represents a hydrogen atom, an aralkyl group optionally having substituent (s), an acyl group, or an acyloxy group; $R^1$, $R^2$, and $R^3$, are same as or different from each other and each of them represents a hydrogen atom, an alkyl group optionally having substituent(s), an alkoxy group optionally having substituent (s), or an amino group optionally having substituent (s); and Y represents a nitrogen atom or CH].

[wherein, ring C', $R^0$, $R^1$, $R^2$, $R^3$, and Y have the same meaning as defined above].

In the compound (I') and compound (II'), the ring C' represents "benzene ring optionally having substituent(s)" or "monocyclic aromatic heterocyclic ring optionally having substituent(s)". Examples of the "monocyclic aromatic heterocyclic ring" include 5- and 6-membered monocyclic aromatic heterocyclic rings such as furan, thiophen, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, and the like. Among these for the ring C', the "benzene ring optionally having substituent(s)" and the "pyridine ring optionally having substituent(s)" are particularly preferable. The position for the "monocyclic aromatic heterocyclic ring" to condense with an imidazole moiety is not particularly limited.

Examples of the substituent for the ring C' include an alkyl group optionally having substituent (s), a halogen atom, a cyano group, a carboxy group, a carbamoyl group, a hydroxy group, an alkoxy group optionally having substituent(s), an acyl group, a carbamoyloxy group, a nitro group, an acyloxy group, an aryl group, an aryloxy group, an alkylthio group, a 5 to 10-membered heterocyclic group, and the like.

As the alkyl group for the "alkyl group optionally having substituent (s)", groups having 1 to 7 carbon atoms are preferable, and examples include a methyl group, an ethyl group, a propyl group, an isopropyl group, a butyl group, an isobutyl group, a sec-butyl group, a tert-butyl group, a pentyl group, a hexyl group, a heptyl group, and the like. Examples of the "substituent" for the "alkyl group optionally having substituent(s)" include a halogen atom, a hydroxy group, a $C_{1-6}$ alkoxy group (e.g., a methoxy group, an ethoxy group, a propoxy group, a butoxy group, etc.), a $C_{1-6}$ alkoxy-carbonyl group (e.g., a methoxy carbonyl group, an ethoxy carbonyl group, a propoxy carbonyl group, etc.), a carbamoyl group, and the like, and the number of the substituents may be from about 1 to 3. When the number of substituent is 2 or more, each substituent may be same as or different from each other.

Examples of the halogen atom include fluorine, chlorine, bromine, and the like, and among them, fluorine is preferable.

As the alkoxycarbonylalkyl group, groups in which each of the alkoxy and alkyl thereof has 1 to 4 carbon atoms are preferable, and examples thereof include a methoxycarbonylmethyl group ($CH_3OOCCH_2$—), a methoxycarbonylethyl group ($CH_3OOCC_2H_4$—), an ethoxycarbonylmethyl group ($C_2H_5OOCCH_2$—), an ethoxycarbonylethyl group ($C_2H_5OOCC_2H_4$—), and the like.

As the alkoxy group for the "alkoxy group optionally having substituent (s)", groups having 1 to 6 carbon atoms are preferable, and examples include a methoxy group, an ethoxy group, a propoxy group, an isopropoxy group, a butoxy group, an isobutoxy group, a pentoxy group, and the like. As the "substituent" for the "alkoxy group optionally having substituent(s)", same ones as the "substituent" for the "alkyl group optionally having substituent (s)" can be exemplified, and the number of substituent is also the same.

As the hydroxyalkyl group, groups in which the alkyl thereof has 1 to 7 carbon atoms are preferable, and examples thereof include a hydroxymethyl group, an 1-hydroxy-propyl group, an 1-hydroxy-ethyl group, an 1-hydroxy-2-methyl-propyl group, and the like.

Examples of the acyl group include a formyl group, an alkylcarbonyl group, an alkoxycarbonyl group, a carbamoyl group, an alkylcarbamoyl group, an alkylsulfinyl group, an alkylsulfonyl group, and the like, and groups having 1 to 4 carbon atoms are preferable.

Examples of the "alkylcarbonyl group" include $C_{1-6}$ alkyl-carbonyl groups (e.g., an acetyl group, a propionyl group, a butyryl group, an isobutyryl group, etc.), and the like.

Examples of the "alkoxycarbonyl group" include a $C_{1-6}$ alkoxy-carbonyl group (e.g., a methoxycarbonyl group ($CH_3OOC$—), an ethoxycarbonyl group ($C_2H_5OOC$—), a propoxycarbonyl group, a butoxycarbonyl group, etc.), and the like, and groups in which the alkoxy thereof has 1 to 4 carbon atoms are preferable.

Examples of the "alkylcarbamoyl group" include N—$C_{1-6}$ alkyl-carbamoyl groups (e.g., a methylcarbamoyl group ($CH_3NHCO$—), an ethylcarbamoyl group ($C_2H_5NHCO$—), etc.), an N,N-di$C_{1-6}$alkyl-carbamoyl group (e.g., an N,N-dimethylcarbamoyl group, an N,N-diethylcarbamoyl group, etc.), and the like, and groups in which the alkyl thereof has 1 to 4 carbon atoms are preferable.

Examples of the "alkylsulfinyl group" include $C_{1-7}$alkylsulfinyl groups (e.g., a methylsulfinyl group, an ethylsulfinyl group, a propylsulfinyl group, an isopropylsulfinyl group, etc.), and the like, and groups having 1 to 6 carbon atoms are preferable.

Examples of the "alkylsulfonyl group" include $C_{1-7}$alkylsulfonyl groups (e.g., a methylsulfonyl group, an ethylsulfonyl group, a propylsulfonyl group, an isopropylsulfonyl group, etc.), and the like.

Examples of the "acyloxy group" include a formyloxy group, an alkylcarbonyloxy group, an alkoxycarbonyloxy group, a carbamoyloxy group, an alkylcarbamoyloxy group, an alkylsulfinyloxy group, an alkylsulfonyloxy group, and the like.

Examples of the "alkylcarbonyloxy group" include $C_{1-6}$alkyl-carbonyloxy groups (e.g., an acetyloxy group, a propionyloxy group, a butyryloxy group, an isobutyryloxy group, etc.) and the like, and groups in which the alkyl thereof has 1 to 4 carbon atoms are preferable.

Examples of the "alkoxycarbonyloxy group" include $C_{1-6}$alkoxy-carbonyloxy groups (e.g., a methoxycarbonyloxy group, an ethoxycarbonyloxy group, a propoxycarbonyloxy group, a butoxycarbonyloxy group, etc.), and the like.

Examples of the "alkylcarbamoyloxy group" include $C_{1-6}$alkyl-carbamoyloxy groups (e.g., a methylcarbamoyloxy group, an ethylcarbamoyloxy group, etc.), and the like.

Examples of the "alkylsulfinyloxy group" include $C_{1-7}$alkylsulfinyloxy groups (e.g., a methylsulfinyloxy group, an ethylsulfinyloxy group, a propylsulfinyloxy group, an isopropylsulfinyloxy group, etc.), and the like.

Examples of the "alkylsulfonyloxy group" include $C_{1-7}$alkylsulfonyloxy groups (e.g., a methylsulfonyloxy group, an ethylsulfonyloxy group, a propylsulfonyloxy group, an isopropylsulfonyloxy group, etc.), and the like.

Examples of the aryl group include $C_{6-14}$ aryl groups (e.g., a phenyl group, a tolyl group, an 1-naphthyl group, a 2-naphthyl group, a biphenyl group, a 2-anthryl group, etc.), and the like.

Examples of the aryloxy group include $C_{6-14}$aryloxy groups (e.g., a phenyloxy group, a tolyloxy group, an 1-naphthyloxy group, a 2-naphthyloxy group, etc.), and the like.

As the alkylthio group, groups in which the alkyl thereof has 1 to 6 carbon atoms are preferable, and examples thereof include a methylthio group, an ethylthio group, a propylthio group, and the like.

Examples of the "5- to 10-membered heterocyclic group" include 5- to 10-membered (preferably 5 or 6 membered) heterocyclic groups having one or more (e.g., 1 to 3) hetero atom(s) selected from a nitrogen atom, a sulfur atom, and an oxygen atom, other than the carbon atom, and specific examples include a 2- or 3-thienyl group, a 2-, 3-, or 4-pyridyl group, a 2- or 3-furyl group, an 1-, 2-, or 3-pyrrolyl group, a 2-, 3-, 4-, 5-, or 8-quinolyl group, an 1-, 3-, 4-, or 5-isoquinolyl group, an 1-, 2-, or 3-indolyl group, and the like. Among these, 5- or 6-membered heterocyclic groups such as an 1-, 2-, or 3-pyrrolyl group are preferable.

The substituent of the ring C' may be substituted by 1 to about 3 to a benzene ring, or may be substituted by 1 to 4 to a substitutable position of a monocyclic aromatic heterocyclic ring. When the number of substituent is 2 or more, each substituent may be same as or different from each other. Of the substituents, a halogen atom, an alkyl group optionally having substituent (s), an alkoxy group optionally having substituent(s), and the like are preferable. It is particularly preferable that the ring C' is not substituted or substituted on the 4- or 5-position with an alkyl group, a halogen atom, a trifluoromethyl group, an alkoxy group or the like among the above substituents.

In the above formula (I') or (II'), the "aralkyl group" for the "aralkyl group optionally having substituent(s)" represented by $R^0$ can be exemplified by a $C_{7-16}$aralkyl group (e.g., $C_{6-10}$aryl $C_{1-6}$alkyl groups such as a benzyl group and a phenethyl group), or the like. As the "substituent" for the "aralkyl group optionally having substituent(s)", same substituents as the "substituent" for the "alkyl group optionally having substituent (s)" can be exemplified, and the number of substituent is from about 1 to 4. When the number of substituent is 2 or more, each substituent may be same as or different from each other.

The "acyl group" represented by $R^0$ can be exemplified by the "acyl group" mentioned above as the substituent of the ring C'.

The "acyloxy group" represented by $R^0$ can be exemplified by the "acyloxy group" mentioned above as the substituent of the ring C'.

The $R^0$ is preferably a hydrogen atom.

Alternatively, the $R^0$ may be an N-protecting group. Examples of the N-protecting group include an alkyl group, an acyl group, an alkoxycarbonyl group, a carbamoyl group, an alkylcarbamoyl group, a dialkylcarbamoyl group, an alkylcarbonylmethyl group, an alkoxycarbonylmethyl group, an alkylsulfonyl group, and the like. The alkyl group preferably has 1 to 5 carbon atoms, and examples include a methyl group, an ethyl group, a propyl group, an isopropyl group, a butyl group, an isobutyl group, a pentyl group, and the like. As the acyl group, same acyl group as the substituent for the ring C' can be exemplified. As the alkoxycarbonyl group, same ones as the substituent for the "alkyl group optionally having substituent (s)" which is exemplified as the substituent for the ring C' can be mentioned. The alkylcarbamoyl group is, represented by the following formula:

in which the alkyl preferably has 1 to 4 carbon atoms, and examples include a methylcarbamoyl group, an ethylcarbamoyl group, a propylcarbamoyl group, an isopropylcarbamoyl group, and the like. The dialkylcarbamoyl group is represented by the following formula:

in which the alkyls preferably have each 1 to 4 carbon atoms, and examples include a dimethylcarbamoyl group, a diethylcarbamoyl group, an N-methyl-N-ethylcarbamoyl group, and the like. The alkylcarbonylmethyl group is represented by the formula: alkyl-CO—CH$_2$—, in which the alkyl preferably has 1 to 4 carbon atoms, and examples include an acetylmethyl group, a propionylmethyl group, and the like. The alkoxycarbonylmethyl group is represented by the formula: alkyl—OCO—CH$_2$—, in which the alkyl preferably has 1 to 4 carbon atoms, and examples include a methoxycarbonylmethyl group, an ethoxycarbonylmethyl group, a propoxycarbonylmethyl group, and the like. The alkylsulfonyl group is represented by the formula: alkyl-SO$_2$—, in which the alkyl preferably has 1 to 4 carbon atoms, and examples include a methylsulfonyl group, an ethylsulfonyl group, a propylsulfonyl group, an isopropylsulfonyl group, and the like.

In the above-mentioned formula (I') or (II'), the "alkyl group optionally having substituent (s)" represented by $R^1$, $R^2$ or $R^3$ can be exemplified by the same group as the "alkyl group optionally having substituent(s)" mentioned above for the substituent of the ring C'. As the alkyl group having halogen atom(s) as a substituent, a fluorine-substituted alkyl group (preferably having 1 to 4 carbon atoms), e.g., a trifluoromethyl group, a 2,2,2-trifluoroethyl group, a 2,2,3,3,3-pentafluoropropyl group, a 1-(trifluoromethyl)-2,2,2-trifluoroethyl group, a 2,2,3,3-tetrafluoropropyl group, a 2,2,3,3,4,4,4-heptafluorobutyl group, etc, can be exemplified.

As the "alkoxy group optionally having substituent(s)" represented by $R^1$, $R^2$, or $R^3$, same group as the "alkoxy group optionally having substituent(s)" mentioned above for the substituent of the ring C' can be exemplified, but it is preferable that the alkoxy group has 1 to 8 carbon atoms (e.g., a methoxy group, an ethoxy group, a propoxy group, an isopropoxy group, a butoxy group, an isobutoxy group, a pentoxy group, a hexyloxy group, a heptyloxy group, an octyloxy group, etc.). As the alkoxy group having halogen atom(s) as a substituent, a fluorine-substituted alkoxy group e.g., a 2,2,2-trifluoroethoxy group, a 2,2,3,3,3-pentafluoropropoxy group, a 1-(trifluoromethyl)-2,2,2-trifluoroethoxy group, a 2,2,3,3-tetrafluoropropoxy group, a 2,2,3,3,4,4,4-heptafluorobutoxy group, a 2,2,3,3,4,4,5,5-octafluoropentoxy group, etc, can be exemplified.

Examples of the "amino group optionally having substituent(s)" represented by $R^1$, $R^2$, or $R^3$ include an amino group, a mono-$C_{1-6}$alkylamino group (e.g., a methylamino group, an ethylamino group, etc.), a mono-$C_{6-14}$arylamino group (e.g., a phenylamino group, an 1-naphthylamino group, a 2-naphthylamino group, etc.), a di-$C_{1-6}$alkylamino group (e.g., a dimethylamino group, a diethylamino group, etc.), a di-$C_{6-14}$arylamino group (e.g., a diphenylamino group), and the like.

The $R^1$ is preferably a $C_{1-6}$alkyl group, a $C_{1-6}$alkoxy group, a $C_{1-6}$alkoxy-$C_{1-6}$alkoxy group, or a di-$C_{1-6}$alkylamino group. The $R^1$ is more preferably a $C_{1-3}$alkyl group or a $C_{1-3}$alkoxy group.

The $R^2$ is preferably a hydrogen atom, a $C_{1-6}$alkoxy-$C_{1-6}$alkoxy group, or a $C_{1-6}$alkoxy group which may be halogenated. The $R^2$ is more preferably a $C_{1-3}$alkoxy group which is halogenated or may be substituted with a $C_{1-3}$alkoxy group.

The $R^3$ is preferably a hydrogen atom or a $C_{1-6}$alkyl group. The $R^3$ is more preferably a hydrogen atom or a $C_{1-3}$alkyl group, but particularly preferably is a hydrogen atom.

In the above-mentioned formula (I') or (II'), Y represents a nitrogen atom or CH, and preferably Y is a nitrogen atom.

Among the compounds represented by the above-mentioned formula (I') or (II'), a compound in which the ring C' is a benzene ring optionally having substituent (s) can be represented by the following formulae (I) and (II):

That is, in the formulae (I) and (II), ring A represents a benzene ring optionally having substituent (s), $R^0$, $R^1$, $R^2$, $R^3$, and Y have the same meaning as in the above-mentioned formulae (I') and (II').

In the formulae (I) and (II), the preferred compound has a ring A which is a benzene ring optionally having 1 or 2 substituent(s) selected from a halogen atom, a $C_{1-4}$alkyl group which may be halogenated, a $C_{1-4}$alkoxy group which may be halogenated, and 5- or 6-membered heterocyclic group; $R^0$ which is a hydrogen atom, an aralkyl group which may be substituted, an acyl group, or an acyloxy group; $R^1$ which is a $C_{1-6}$alkyl group, a $C_{1-6}$alkoxy group, a $C_{1-6}$alkoxy-$C_{1-6}$alkoxy group, or a di-$C_{1-6}$alkylamino group; $R^2$ which is a hydrogen atom, a $C_{1-6}$alkoxy-$C_{1-6}$alkoxy group, or a $C_{1-6}$alkoxy group which may be halogenated; $R^3$ which is a hydrogen atom or a $C_{1-6}$alkyl group; and Y which is a nitrogen atom.

When the compounds (I) and (II) are described in more detail, it is particularly preferable that the ring A is either non-substituted or substituted on the 4- or 5-position with a methoxy group or a trifluoromethyl group, $R^0$ is a hydrogen atom, $R^1$ and $R^3$ are same as or different from each other and each a hydrogen atom or a methyl group, and $R^2$ is a fluorinated alkoxy group having 2 to 5 carbon atoms.

In addition, the target oxidized compound (II) is particularly preferably the compound represented by the formula (IIa):

[wherein, $R^1$ represents a $C_{1-3}$alkyl group or a $C_{1-3}$alkoxy group; $R^2$ represents a $C_{1-3}$alkoxy group which is halogenated or may be substituted with a $C_{1-3}$alkoxy group; $R^3$ represents a hydrogen atom or a $C_{1-3}$alkyl group; $R^4$ represents a hydrogen atom, a $C_{1-3}$alkoxy group which may be halogenated, or a pyrrolyl group (e.g., 1-, 2- or 3-pyrrolyl group)].

In the formula (IIa), it is particularly preferable that the compound has $R^1$ which is a $C_{1-3}$alkyl group, $R^2$ which is a $C_{1-3}$alkoxy group which may be halogenated, $R^3$ which is a hydrogen atom, and $R^4$ which is a hydrogen atom or a $C_{1-3}$alkoxy group which may be halogenated.

Specific examples of the compound (II) can be exemplified by the following compounds:
2-[[[3-methyl-4-(2,2,2-trifluoroethoxy)-2-pyridyl]methyl]sulfinyl]-1H-benzimidazole (lansoprazole),
2-[[(3,5-dimethyl-4-methoxy-2-pyridyl]]methyl]sulfinyl]-5-methoxy-1H-benzimidazole (omeprazole),
2-[[[4-(3-methoxypropoxy)-3-methyl-2-pyridyl]methyl]sulfinyl]-1H-benzimidazole (rabeprazole).sodium salt,
5-difluoromethoxy-2-[[(3,4-dimethoxy-2-pyridyl)methyl]sulfinyl]-1H-benzimidazole (pantoprazole),
2-[[[2-(methylisobutylamino)phenyl]methyl]sulfinyl]-1H-benzimidazole (leminoprazole),
2-[(RS)-[(4-methoxy-3-methylpyridin-2-yl)methyl]sulfinyl]-5-(1H-pyrrol-1-yl)-1H-benzimidazole (ilaprazole), and the like.

In the above-mentioned formula (II'), an imidazopyridine compound of which the ring C' is apyridine ring is also preferable. Such compound can be exemplified by 5-methoxy-2-[[(4-methoxy-3,5-dimethyl-2-pyridyl)methyl]sulfinyl]-1H-imidazo[4,5-b]pyridine (tenatoprazole (TU-199)).

The above-mentioned compounds (II'), (II), and (IIa) may be provided as a racemate, and may be an optically active substance such as R-form and S-form. For example, optically active substances of lansoprazole, that is, optically active substances such as (R)-2-[[[3-methyl-4-(2,2,2-trifluoroethoxy)-2-pyridyl]methyl]sulfinyl]-1H-benzimidazole (R-form of lansoprazole) and (S)-2-[[[3-methyl-4-(2,2,2-trifluoroethoxy)-2-pyridyl]methyl]sulfinyl]-1H-benzimidazole (S-form of lansoprazole) are particularly preferable for the invention. In addition, it is usually preferable that lansoprazole, lansoprazole R-form, and lansoprazole S-form are in crystal, but may also be amorphous without being limited by a crystal.

As the salts of the compounds (I'), (II'), (I), (II), and (IIa), pharmaceutically acceptable salts are preferable, and examples include salts with an inorganic base, salts with an organic base, salts with a basic amino acid, and the like.

Preferred examples of the salts with an inorganic base include alkali metal salts such as a sodium salt and a potassium salt; alkaline earth metal salts such as a calcium salt and a magnesium salt; ammonium salts, and the like.

Examples of the salts with an organic base preferably include salts with alkylamine (trimethylamine, triethylamine, etc.), heterocyclic amine (pyridine, picoline, etc.), alkanolamine (ethanolamine, diethanolamine, triethanolamine, etc.), dicyclohexylamine, N,N'-dibenzylethylenediamine, and the like. Specific examples of the salts with an organic base preferably include salts with trimethylamine, triethylamine, pyridine, picoline, 2,6-lutidine, ethanolamine, diethanolamine, triethanolamine, tromethamine[tris(hydroxymethyl)methylamine], t-butylamine, cyclohexylamine, dicyclohexylamine, N,N'-dibenzylethylenediamine, and the like.

Examples of the salts with a basic amino acid preferably include salts with arginine, lysine, ornithine, and the like.

Among these salts, the alkali metal salts and the alkaline earth metal salts are preferable. In particular, the sodium salt is preferable.

In the invention, the compound (II') is preferably lansoprazole, omeprazole, rabeprazole, pantoprazole, leminoprazole, ilaprazole, tenatoprazole (TU-199), or the like, or optically active substance thereof or pharmaceutically acceptable salt thereof, and is more preferably lansoprazole or the optically active substance thereof, particularly the R-form.

The oxidizing agent useful for the invention is not limited, and commonly used oxidizing agent can be employed. For example, the oxidation can be carried out according to the method disclosed in Japanese Unexamined Patent Publication No. S61-50978, Japanese Unexamined Patent Publication No. H01-131176, U.S. Pat. No. 4,628,098, Japanese Unexamined Patent Publication No. H10-195068, Pamphlet of International Publication WO 98/21201, Japanese Unexamined Patent Publication No. S52-62275, or Japanese Unexamined Patent Publication No. 54-141783, or a method analogous thereto. For the oxidation reaction to give the compound (II') from the compound (I'), oxidation carried out using hydrogen peroxide as an oxidizing agent is particularly preferable among others. In addition, it is preferable to use a vanadium compound as a catalyst.

As the vanadium compound, vanadium pentoxide ($V_2O_5$), sodium metavanadate ($NaVO_3$), ammonium metavanadate ($NH_4VO_3$), vanadyl acetylacetonate [$(CH_3COCH_2COCH_3)_2VO$], and the like can be exemplified, and preferably vanadium pentoxide, sodium metavanadate, and vanadyl acetylacetonate are used.

The used amount of the vanadium compound is in the range of usually about 0.01 to 10 mol %, preferably about 0.05 to 2 mol %, and particularly preferably about 0.1 to 0.5 mol %, to the compound (I'). As hydrogen peroxide, an aqueous hydrogen peroxide solution is usually used, but a solution state of an organic solvent such as n-butyl alcohol may also be used. The concentration of hydrogen peroxide to be used is in the range of usually 10 to 70% and preferably 20 to 40%, but is not particularly limited by these ranges.

Hydrogen peroxide may be usually used in a slightly excessive amount, preferably from about 1 to 3 equivalent amount, and more preferably from about 1 to 1.5 equivalent amount, to 1 equivalent amount of the compound (I'). As the solvent to be used in the reaction, halogenated hydrocarbons such as chloroform and dichloromethane, ethers such as tetrahydrofuran and dioxane, amides such as dimethylformamide, alcohols such as methanol, ethanol, and isopropanol, ketones such as acetone and methylethylketone, nitrites such as acetonitrile, water, or the like can be mentioned, and methanol, ethanol, acetone, and acetonitrile are preferably used and ethanol is particularly preferably used. These solvents may be used alone or in combination. The amount of a solvent to be used in the reaction is from about 0.5 to 10 L and preferably from about 1 to 5 L, per 1 mol of the compound (I'), but is not particularly limited by these ranges.

The reaction temperature is under ice-cooling to near the boiling point of the solvent to be used, usually is from under ice-cooling to about 40° C., and more preferably from about 15 to 30° C. The reaction time is usually from about 0.5 to 24 hours, and more preferably from about 1 to 8 hours.

The target compound (II') produced by the above oxidation reaction usually precipitates as a crystal from the reaction solution, thus excessive hydrogen peroxide after the reaction can be decomposed by adding an oxidation reaction terminating agent (e.g., an aqueous sodium thiosulfate solution, etc.), and the precipitated crystals can be filtered to be isolated, but if necessary, the solvent extraction with chloroform or the like may be carried out, followed by concentration to be isolated. In addition, the isolated crystals can be purified by conventional means such as recrystallization, chromatography, and the like, if necessary. The optically active substance of the compound (II') can be obtained by optically resolving a racemate of the compound (II') produced by the above oxidation reaction, with the use of the optical resolution method (fractional recrystallization method, a chiral column method, a diastereomer method, a method using a microorganism or enzyme, etc.), or can be directly obtained by carrying out an asymmetrical oxidation for the above-mentioned oxidation reaction. In addition, R-form of lansoprazole can be produced with the above oxidation reaction, for example, in accordance with the production method disclosed in Pamphlet of International Publication WO 00/78745, Pamphlet of International Publication WO 01/83743, and the like.

The starting compound (I') can be produced, for example, in accordance with the method disclosed in U.S. Pat. No. 4,255,431, European Patent Publication No. 45,200, European Patent Publication No. 74,341, European Patent Publication No. 80,602, European Patent Publication No. 5,129, European Patent Publication No. 174,726, European Patent Publication No. 175,464, United Kingdom Patent Publication No. 2,134,523A, and the like.

In the invention, an electric potential of an oxidation reaction solution for producing an oxidized compound is measured, and an end point of the oxidation reaction is determined on the basis of a predefined decrease of the electric potential. Therefore, it is preferable to use an oxidation reduction potential (ORP) meter for an electric potential measurement of the oxidation reaction solution. In addition, a reactor for carrying out the oxidation reaction is not particularly limited, and can be appropriately selected from various reactors according to the target oxidized compound (oxidation reaction).

The oxidation reaction in the invention is not particularly limited, and can be exemplified by oxidation reaction of sulfide to sulfoxide, oxidation reaction of alcohol to ketone, oxidation reaction of aldehyde to carboxylic acid, oxidation reaction of amine to nitroso, oxidation reaction of phosphine to phosphine oxide, or the like, and preferably exemplified by the oxidation reaction of sulfide (e.g., the imidazole compound represented by the above-mentioned formula (I) or (I') or salts thereof) to sulfoxide (e.g., an oxidized compound of the imidazole compound represented by the above-mentioned formula (II) or (II') or salts thereof).

As the industrial practice method of the invention, there mentioned a system as a preferred embodiment, in which a sensor (submersion type, etc.) for the oxidation reduction potential (ORP) meter is attached to the reactor for carrying out the oxidation reaction, the oxidation reduction potential of the oxidation reaction solution in the reactor is monitored at all time, a highest point for the electric potential to reach is determined by a program, and then a point where the electric potential is rapidly decreased is determined as the end point of the oxidation reaction. In addition, the program is preferably incorporated in the operation of informing the operator that the reaction is finished and stopping the reaction.

The termination of the oxidation reaction can be carried out, for example, by removing a starting material such as an oxidizing agent provided in excess, or the like. For example, for the oxidation reaction using hydrogen peroxide as an oxidizing agent to produce lansoprazole of which $R^2$ is $OCH_2CF_3$, $R^1$ is $CH_3$, $R^3$ is H, $R^0$ is H, and ring C' is a non-substituted benzene ring in the formula for the compound (II'), the oxidation reaction is preferably terminated by introducing an aqueous sodium thiosulfate solution (oxidation reaction terminating agent) to the oxidation reaction solution to decompose the unreacted hydrogen peroxide.

Examples of the oxidation reaction terminating agent include sodium sulfite, sodium hydrogensulfite, and the like, in addition to the aforementioned aqueous sodium thiosulfate solution.

Figure 1:
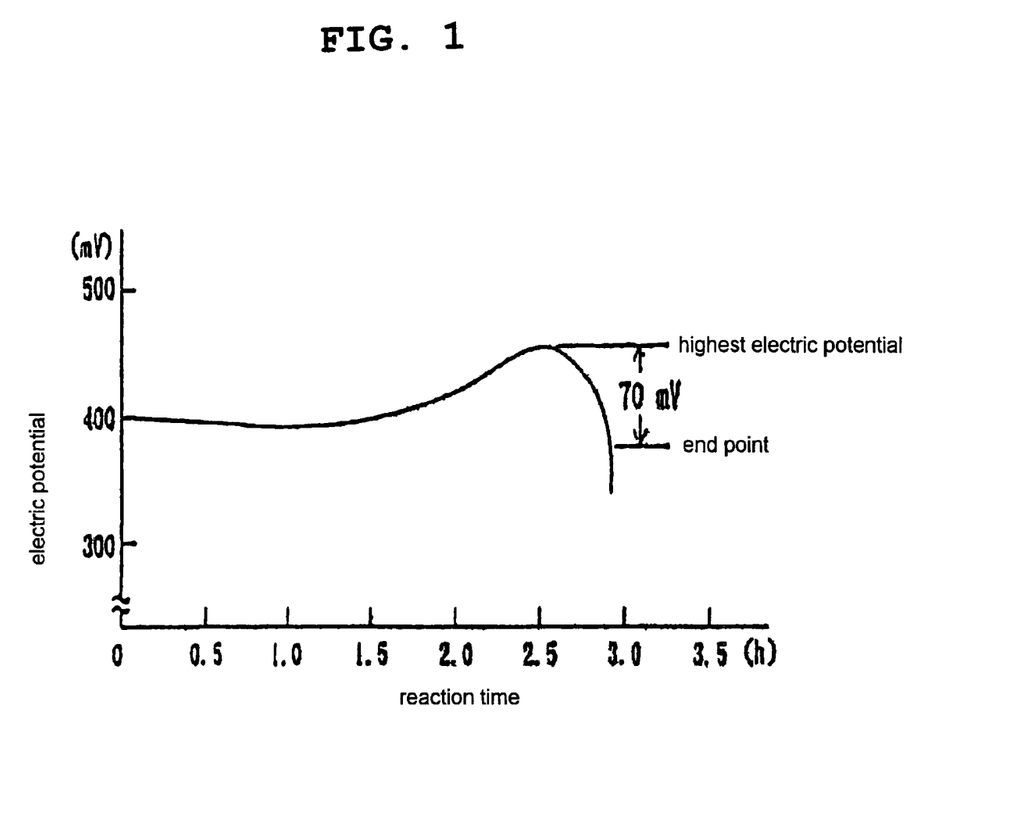
FIG. 1 is a chart showing the change in the oxidation reduction potential of the oxidation reaction solution for an oxidation reaction which oxidizes a starting compound, SUL, with hydrogen peroxide using vanadyl acetylacetonate as a catalyst to obtain lansoprazole.

For producing lansoprazole by using 2-(((3-methyl-4-(2,2, 2-trifluoroethoxy)-2-pyridyl)methyl)thio)benzimidazole monohydrate (hereinafter, also may be referred to as SUL) as a starting compound (I'), ethanol as a reaction solvent, and vanadyl aceylacetonate as a catalyst, and oxidizing with hydrogen peroxide, when the oxidizing agent (hydrogen peroxide) is added dropwise over 10 to 30 minutes, then reacted at 20 to 21° C., and the oxidation reduction potential of the reaction solution is monitored with an ORP meter, the electric potential follows the time course shown in FIG. 1. That is, the electric potential gradually increases, and when drops by about 70 mV after reaching to the highest electric potential, this dropped point can be determined as the reaction end point. Accordingly, it is confirmed that the end point corresponds to a point where the spot size of the starting material SUL comes within the range of about 1 to 3% of the SUL standard solution when the reaction solution is observed with TLC, the starting compound SUL is almost consumed, and that the oxidation is completed.

In the invention, any ORP meter model can be employed, but in an industrial production, a meter in which an ORP transmitter can be equipped with an ORP sensor is preferable in order to enable a computational control. In particular, when a microprocessor-equipped ORP transmitter is used, a sensor defect, etc. can be monitored during the ORP measurement, thus is suitable for a large-scale apparatus in a factory. As the preferred ORP meter, for example, OR8EFG-PT-05-TT2-NN * A manufactured by Yokogawa Electric Corp. can be mentioned.

Figure 2:
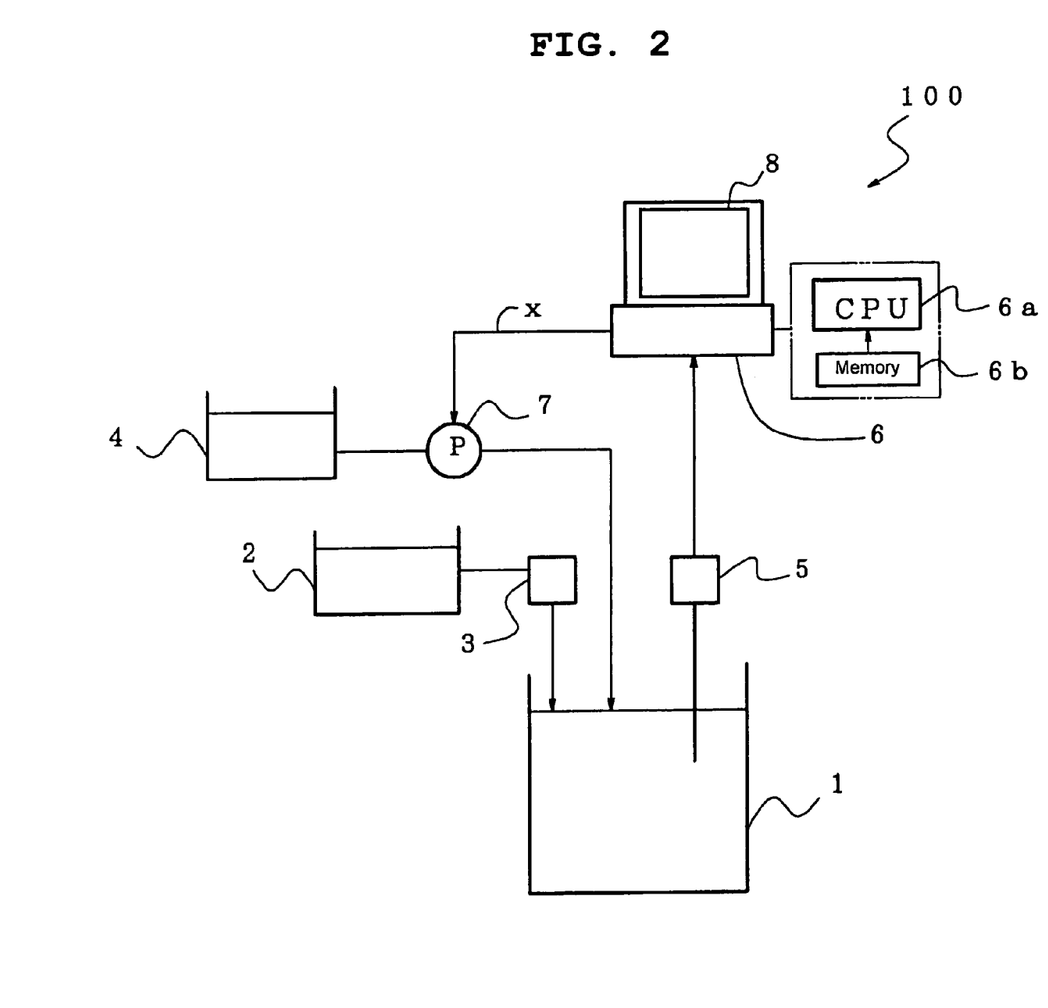
FIG. 2 is a diagram schematically showing an exemplary apparatus for producing an oxidized compound of the invention. Herein, symbols in the diagram indicate as follows. 1: reactor, 2: oxidizing agent tank, 3: flow rate regulator, 4: oxidation reaction terminating agent tank, 5: ORP meter, 6: computer, 7: automatic valve, 8: monitor, 100: oxidized compound production system.

FIG. 2 shows a specific example of an oxidized compound production system carrying out the method of the invention in an industrial scale.

The system 100 is constructed in the manner to dropwisely introduce an oxidizing agent stored in the oxidizing agent tank 2 by the flow rate regulator 3 into the reactor 1 which accommodates a starting compound (solution), and to supply an oxidation reaction terminating agent stored in the oxidation reaction terminating agent tank 4 in a predetermined amount to the reactor 1. When the temperature condition of the reactor 1 and the like are set to predetermined conditions and an oxidizing agent in the oxidizing agent tank 2 is dropwisely introduced into the reactor 1, the oxidation reaction initiates and proceeds to produce an oxidized compound. Then, when an oxidation reaction terminating agent from the oxidation reaction terminating agent tank 4 is introduced into the reactor 1, the oxidation reaction terminates, and thereafter the reaction solution containing the oxidized compound is drained out to the processing unit for a next step by a draining apparatus not shown in the figure.

The reactor 1 is provided with the ORP meter 5, and this ORP meter 5 detects the oxidation reduction potential of the reaction solution in the reactor 1 from the start of the oxidation reaction, and the detected values are inputted into the computer 6. The computer 6 functions as a determination means which at all time monitors the inputted detected value of the oxidation reduction potential and determines the end point of the oxidation reaction on the basis of the inflection point (highest electric potential) with the time course. The computer 6 performs the calculation for detecting the highest electric potential of the oxidation reduction potential and the calculation for detecting the amount of an electric potential dropped from the highest electric potential, and compares the dropped amount of the electric potential with the threshold value preliminarily set, so as to determine the endpoint of the oxidation reaction. Here, the threshold value means the difference (amount of electric potential dropped) between the highest electric potential reached of the reaction solution and the electric potential at the end point of the oxidation reaction in the oxidation reaction carried out by the reactor, which is obtained by practically measuring the history of the oxidation reduction potential of the oxidation reaction solution in advance and then relating the history to the end point of the oxidation reaction confirmed from a quenching amount of the starting compound with TLC or the like. For example, in the aforementioned case of producing lansoprazole by oxidizing SUL with hydrogen peroxide, the dropped electric potential amount after reaching the highest electric potential which gives the end point of the oxidation reaction is 70 mV. The computer 6 has a CPU 6*a* for carrying out the determination process and a memory 6*b* for storing the program.

The monitor 8 is a displaying means for displaying the history of the oxidation reduction potential monitored by the computer 6, and the operator can observe the change of the oxidation reduction potential of the oxidation reaction solution over a time course and the reaction end point with the monitor 8. The chart in FIG. 1 is an exemplary output chart of the oxidation reduction potential displayed on the monitor 8. The operator can swiftly stop the oxidation reaction by giving the order to the automatic valve 7 to supply an oxidation reaction terminating agent stored in the oxidation reaction terminating agent tank 4 to the reactor 1 after confirming the end point of the oxidation reaction with the monitor 8. In addition, there may be provided with an informing means (not shown) such as a lamp or a buzzer which lights or alarms at the same time as the end point of the oxidation reaction is determined, thereby allowing the operator to more precisely recognize the end point of the oxidation reaction.

Further, if the computer 6 is allowed to output a command signal x to the automatic valve 7 so as to supply an oxidation reaction terminating agent in the oxidation reaction terminating agent tank 4 to the reactor 1 when the end point of the oxidation reaction is determined, the oxidation reaction can be more promptly stopped, moving on to the next step is more swiftly done, and the production efficiency can be improved.

In the invention, as the next step after terminating the oxidation reaction, for example, a process for isolating insolubles by filtering the liquid in which precipitated crystals of the oxidized compound are dissolved, or the like can be carried out. In the case, the concentration process by a solvent extraction of the oxidation reaction solution or the like, or the like may also be carried out, if necessary.

As described above, the invention is particularly suitable for the oxidation reactions for obtaining the compound (II') from the compound (I') using an oxidizing agent, and among these particularly suitable for the oxidation reaction producing lansoprazole by oxidizing SUL with hydrogen peroxide.

The invention also relates to a method of producing a remarkably stable crystal of an imidazole compound represented by the above general formula (II') or a salt thereof.

For the method of producing the remarkably stable crystal, the compound (II') is preferably a racemate, and it may be difficult to be directly applied to the optically active substance such as R-form and S-form of lansoprazole which has a different physicochemical characteristic to the racemate.

The production method is characterized in that the remarkably stable crystal is produced from a solvate of the imidazole compound represented by the general formula (II') or a salt thereof by suspending the solvate into a solution having a pH of about 7 to 11 or into a solution containing water, an organic solvent (e.g., alcohol), and a basic substance.

The solvate of the imidazole compound represented above by the general formula (II') or a salt thereof is not particularly limited in its production method and can be produced according to a method known per se, but preferably produced with remarkably high production efficiency by oxidizing an imidazole compound represented above by the general formula (I') or a salt thereof according to the above-mentioned method of producing the oxidized compound of the present invention, and then crystallizing from an organic solvent or an aqueous organic solvent. When an organic solvent such as alcohols e.g., methanol, ethanol, propanol, n-butanol, isobutanol, etc., ketones e.g., acetone, methylethylketone, etc., esters e.g., ethyl acetate, etc., sulfoxides e.g., dimethylsulfoxide, etc., and amides e.g., dimethylformamide, etc., is used, a crystal of solvate containing such solvent is obtained, and when a mixed solvent of alcohols e.g., methanol, ethanol, n-butanol, isobutanol, etc., ketones e.g., acetone, methylethylketone, etc., esters e.g., ethyl acetate, etc., sulfoxides e.g., dimethylsulfoxide, etc., amides e.g., dimethylformamide, etc., or the like and water is used, a crystal of solvate of water and organic solvent containing each 1 molar equivalent of such organic solvent and water is obtained.

As the organic solvent included in the above solution, alcohols (e.g., methanol, ethanol, propanol, etc.) are preferable, and ethanol is particularly preferable. Examples of the basic substance included in the above solution include amine such as ammonia and triethylamine, alkali metal hydroxide such as sodium hydroxide, calcium hydroxide, sodium carbonate, and sodium hydrogen carbonate, alkaline earth metal hydroxide, alkali metal carbonate, alkaline earth metal carbonate, alkali metal hydrogencarbonate, and the like, and ammonia is preferably used among them. It is preferable that the pH of the above solution is in the range of about 7 to 11, and preferably in the range of about 8 to 9, by adding the basic substance. In addition, the content of the organic solvent (preferably, alcohol) and the basic substance with respect to water in the above solution is not particularly limited, as long as it is the amount such that pH of the solution is ranging from about 7 to 11. For the preferred operational condition, the ratio of a water-organic solvent (preferably, alcohol) is from 10 to 500:1 (weight ratio), preferably from 20 to 200:1 (weight ratio), and more preferably from 20 to 100:1 (weight ratio). The ratio of a water-basic substance-organic solvent (preferably, alcohol) is from 10 to 500:0.0001 to 0.5:1 (weight ratio), preferably from 20 to 200:0.001 to 0.5:1 (weight ratio), and more preferably from 20 to 100:1 (weight ratio). For example, when ammonia is used as a basic substance, the ratio of a water-ammonia water (25%)-organic solvent (preferably, alcohol) is from 10 to 500:0.005 to 0.5:1 (weight ratio), preferably from 20 to 200:0.005 to 0.1:1 (weight ratio), and more preferably from 20 to 100:0.005 to 0.1:1 (weight ratio). Although the content of alcohol with respect to water is very small in quantity (e.g., alcohol included as a crystalline solvent in the solvate or alcohol adhered on the surface of a crystal of the solvate (by the process of washing the crystal, or the like)), there is still an action and effect of improving the stability of the crystal to be obtained (crystal substantially not containing a solvent). On the other hand, when the content of alcohol with respect to water is increased beyond the aforementioned range, the improvement in stability tends to become over the limit, and more likely to lower the quality of the crystal to be obtained.

Further, the alcohol content in the solution for suspending a crystal can be appropriately adjusted within the above range as described below, thus the action and effect of further improving the stability can be exhibited.

The temperature of the above solution and the stirring period during suspending a solvate to the solution can be appropriately selected, but specifically, for example, the temperature of the solution is preferably from 20 to 40° C. and more preferably from 24 to 30° C., and the stirring period is preferably from 10 to 120 minutes and more preferably from 30 to 60 minutes.

For the method of producing a remarkably stable crystal of the present invention, the imidazole compound represented by the general formula (II') or a salt thereof is preferably lansoprazole or a salt thereof.

By means of the aforementioned suspending process, a crystal form transformation of a solvate occurs, and the solvent is removed during this transformation. In the suspending process, the decomposition of a crystal during the crystal form transformation can be prevented by including a basic substance into a solution in which the solvate is suspended, and the stability of the crystal to be obtained can be improved by appropriately adjusting the alcohol content within the above range.

The present inventors have found during various investigations to complete the method of the invention that the SUL (compound of which $R^2$ is $OCH_2CF_3$, $R^1$ is $CH_3$, $R^3$ is H, $R^0$ is H, and C' is a non-substituted benzene ring in the general formula (I')) which is a starting compound of lansoprazole can be obtained preferably by a series of reactions as shown in the following formula, and particularly, that the yield is improved when the condensation reaction at the second stage is carried out by adjusting the pH to 11.0-11.5, thereby being industrially advantageous.

Since the compound with less byproducts produced by an overreaction and higher purity can be obtained as the oxidized compound obtainable in the invention, the invention can be suitably applied for a large-scale production of the compound useful as particularly a drug, and the like. For example, when a proton pump inhibitor typified by lansoprazole, an optically active substance thereof, or the like is obtained as a target product, this product can be employed as an antiulcer agent, an anti *H. pylori* agent, or the like, for example, in accordance with the method disclosed in Japanese Unexamined Patent Publication No. S61-50978 or Japanese Unexamined Patent Publication No. H03-173817.

EXAMPLES

Hereinafter, Examples of the invention will be explained.

Example 1

Production Method of 2-(((3-methyl-4-(2,2,2-trifluoroethoxy)-2-pyridyl)methyl)thio)benzimidazole monohydrate]

2-hydroxymethyl-3-methyl-4-(2,2,2-trifluoroethoxy)pyridine (87.4 kg) was dissolved in methylene chloride (655 L), thionyl chloride (41.1 L) was added to the solution, and the mixture was heated under reflux for about 60 minutes. Water (183 kg) was added to the mixture, and the mixture was concentrated. To the residue were added methanol (656 L) and 2-benzimidazolethiol (59.8 kg), then the pH was adjusted to 11.0-11.5 with a 30% aqueous solution of sodium hydroxide, and the mixture was reacted for 30 minutes. To the reaction solution was added water (524 kg) and the mixture was recrystallized. pH was adjusted to 8.5-10.0 with 35% hydrochloric acid, and then the precipitated crystals were filtered. The crystals were washed with an aqueous methanol solution (methanol:water=5:5 (weight ratio)) and water, and then dried to obtain 141.6 kg of 2-(((3-methyl-4-(2,2,2-trifluoroethoxy)-2-pyridyl)methyl)thio)benzimidazole monohydrate as white crystals (yield: 96.5%).

Example 2

Production of (+/−)-2-(((3-methyl-4-(2,2,2-trifluoroethoxy)-2-pyridyl)methyl)sulfinyl)benzimidazole 2-(((3-methyl-4-(2,2,2-trifluoroethoxy)-2-pyridyl)methyl)thio)benzimidazole monohydrate (141.6 kg) was dissolved in ethanol (1164 L), and vanadyl acetylacetonate (0.44 kg) wetted with ethanol (about 200 mL) was added to the solution. Thereafter, a 35% hydrogen peroxide solution (42 L) was added dropwise to the mixture at 16 to 22° C., and then the mixture was reacted at 18 to 24° C. until the electric potential dropped by 70 mV from the highest electric potential of the ORP (oxidation reduction potential) meter. After the electric potential dropped by 70 mV and the reaction was completed, an aqueous sodium thiosulfate solution (12.7 kg/127 L) was added to the reaction solution, and the mixture was stirred. Triethylamine (7 L) was added to the mixture, the precipitated crystals were dissolved with heating at about 50 to 55° C., the insolubles were removed by filtration with heating, and the filtrate was cooled to crystallize. The crystals were filtered, and washed with a cooled aqueous ethanol solution (ethanol:water=9:1 (weight ratio)).

Subsequently, to the obtained crystals were added a 25% aqueous ammonia solution (0.9 L) and an aqueous ethanol solution (ethanol:water=9:1 (weight ratio), 864 L), the mixture was heated under stirring to dissolve the crystals, and cooled to crystallize. The crystals were filtered, and washed with a cooled aqueous ethanol solution (ethanol:water=9:1 and 7:3 (weight ratio)) to obtain wet crystals of a solvate of ethanol-water of (+/−)-2-(((3-methyl-4-(2,2,2-trifluoroethoxy)-2-pyridyl)methyl)sulfinyl)benzimidazole (lansoprazole).

To the obtained wet crystals, a mixed solution (pH of about 9) of water (1043 kg) and a 25% aqueous ammonia solution (about 17 mL) was added, and the obtained suspension was stirred at 24 to 30° C. for about 60 minutes. The crystals were filtered, washed with water, and air dried to obtain 107.5 kg of (+/−)-2-(((3-methyl-4-(2,2,2-trifluoroethoxy)-2-pyridyl)methyl)sulfinyl)benzimidazole (lansoprazole) as white crystals (yield: 76.3%). This crystal is referred to as lansoprazole I type crystal. The obtained crystals are stable.

Example 3

Production of (+/−)-2-(((3-methyl-4-(2,2,2-trifluoroethoxy)-2-pyridyl)methyl)sulfinyl)benzimidazole To about 190 kg of the wet crystals of the solvate of ethanol-water of (+/−)-2-(((3-methyl-4-(2,2,2-trifluoroethoxy)-2-pyridyl)methyl)sulfinyl)benzimidazole obtained according to the method in EXAMPLE 2 was added a mixed solution (pH of about 9) of water (about 1043 kg), a 25% aqueous ammonia solution (about 500 mL), and ethanol (the composition of the mixed solution was adjusted to water:25% aqueous ammonia solution:ethanol=about 19:0.008:1 (weight ratio)), and thus obtained suspension was stirred at 24 to 30° C. for about 60 minutes. The crystals were filtered, washed with water, and air dried to obtain about 110 kg of (+/−)-2-(((3-methyl-4-(2,2,2-trifluoroethoxy)-2-pyridyl)methyl)sulfinyl)benzimidazole (lansoprazole) as white crystals (yield: 94%).

Test 1

The stability of the crystals of the solvate of lansoprazole (hereinafter, referred to as lansoprazole (1)) obtained by vacuum drying the wet crystals of the solvate of ethanol-water of lansoprazole obtained according to the method in EXAMPLE 2, was compared to the stability of the white crystals of lansoprazole (hereinafter, referred to as lansoprazole (2)) obtained according to the method in EXAMPLE 3. The results for each of 3 samples for the lansoprazoles (1) and (2) are shown in the Table 1 below.

TABLE 1

| Lansoprazole | Initial Content | Content after stored for 6 months at 40° C. | Residual ratio after stored for 6 months at 40° C. |
|---|---|---|---|
| (1) | 99.2% | 90.6% | 91.3% |
| (1) | 99.3% | 84.1% | 84.7% |
| (1) | 99.1% | 86.0% | 86.8% |
| (2) | 99.7% | 99.6% | 99.9% |

TABLE 1-continued

| Lansoprazole | Initial Content | Content after stored for 6 months at 40° C. | Residual ratio after stored for 6 months at 40° C. |
|---|---|---|---|
| (2) | 99.8% | 99.8% | 100.0% |
| (2) | 99.8% | 99.8% | 100.0% |

Herein, the "content" in Table 1 refers to the content of lansoprazole in lansoprazole crystals expressed in wt %, and was measured by HPLC technique (analyzed under each of following conditions: for (1), Column: NOVA PAK, C18, 3.9×150 mm, Temperature: constant temperature of around 25° C., Mobile phase: solution prepared by adjusting the pH of methanol:water:triethylamine (weight ratio=60:40:1) with phosphoric acid to 7.0, Flow rate: 0.5 ml/min, Detector: UV 285 nm, and for (2), Column: CAPCELL PAC, C18, SG120, 4.6×250 mm, Temperature: constant temperature of around 25° C., Mobile phase: solution prepared by adjusting the pH of acetonitrile:water:triethylamine (weight ratio=40:60:1) with phosphoric acid to 7.0, Flow rate: 1 ml/min, Detector: UV 285 nm). The "residual ratio after stored for 6 months at 40° C." was calculated by [(Content after stored for 6 months at 40° C.)/(Initial Content)]×100(%).

From the Table 1, followings are understood. The initial content of lansoprazole (2) is slightly higher than that of lansoprazole (1), but it is almost the same. However, when the content after being stored for 6 months at 40° C. was compared, the content of lansoprazole (2), which was subjected to suspending in the solution of pH=about 9 which contains water, ethanol, and ammonia, was almost unchanged from the initial content (residual ratio was either 100% or almost 100%), where the content of lansoprazole (1), which was not subjected to suspending in the solution of pH=about 9 which contains water, ethanol, and ammonia, was notably reduced from the initial content (residual ratio was from about 84 to 91%).

As above, it is appreciated that the lansoprazole (2) is the crystal having more excellent stability as compared to the lansoprazole (1).

Test 2

In the method according to EXAMPLE 3, the amount of ethanol added to the mixed solution in which the wet crystals of the solvate of ethanol-water of lansoprazole are suspended was changed, and the stability of thus obtained crystals was compared.

The crystals obtained from each of mixed solution systems shown in Table 2 below were each dissolved in dimethylformamide just after the preparation and after stored at 60° C. for 15 days, and the absorbance (390 nm) of thus obtained solutions of crystals was measured. The degree of coloration was compared as an indicator of the crystal stability. The results are shown as a relation between the added amount of ethanol and the change in absorbance (390 nm) of solutions of crystals, in the Table 2 below.

The absorbance of the solution prepared by dissolving 1 g of crystals into 10 mL of dimethylformamide was measured with the use of a spectral photometer (Jasco No. 0214332).

In addition, the pH of each mixed solution in which crystals are suspended was adjusted to about 9 with an aqueous ammonia solution.

TABLE 2

| Ethanol content to be added to mixed solution (water:ethanol) (weight ratio) | Ethanol concentration of mixed solution | Absorbance of solution of crystals just after preparation | Absorbance of solution of crystals after stored at 60° C. for 15 days | Change in Absorbance*2 |
|---|---|---|---|---|
| Ethanol non-added | 2.3 wt %*1 | 0.046 | 1.703 | 1.657 |
| About 160:1 | 4.1 wt % | 0.054 | 1.135 | 1.081 |
| About 40:1 | 5.7 wt % | 0.056 | 0.964 | 0.908 |

*1 derives from ethanol provided as a crystal solvent and ethanol adhered on a crystal surface
*2 change in absorbance = [Absorbance of solution of crystals after stored at 60° C. for 15 days] − [Absorbance of solution of crystals just after preparation]

From the Table 2, it is appreciated that the amount of absorbance change decreased, that is, the degree of crystal coloration was reduced, as the added amount of ethanol to the mixed solution in which crystals are suspended was increased.

As above, it is appreciated that the stability of crystals was further improved by increasing the amount of ethanol to be added to the mixed solution in which crystals are suspended.

INDUSTRIAL APPLICABILITY

As is clear from the above description, an end point of an oxidation reaction can be simply determined by the method of producing an oxidized compound of the invention, thus moving on to the next step after terminating the oxidation reaction is more swiftly achieved. In addition, since it is possible to obtain a production system capable of achieving a computer automation and carrying out an operation to stop the reaction immediately after determining the end point of the oxidation reaction, the production efficiency of the oxidized compound in an industrial production process can be greatly improved.

The present application is based on Japanese Patent Application No. 2004-265717 filed in Japan and the contents of which are incorporated in full herein by this reference.

The invention claimed is:

1. A method of producing a crystal of lansoprazole, or a salt thereof, the method comprising removing the solvent by suspending a solvate of lansoprazole or a salt thereof into a solution containing water, alcohol, and a basic substance, wherein the ratio of a water-basic substance-alcohol is from 10 to 500:0.0001 to 0.5:1 (weight ratio).

2. The production method according to claim 1, wherein the basic substance is ammonia.

3. The production method according to claim 2, wherein the pH of the solution containing water, alcohol, and ammonia is about 8 to 9.

* * * * *